United States Patent
White

(10) Patent No.: US 7,221,450 B2
(45) Date of Patent: May 22, 2007

(54) DUAL WAVELENGTH OPTICAL ANALYSER

(75) Inventor: Julian White, Cambridge (GB)

(73) Assignee: Genapta Ltd, Cambridge (GB)

( * ) Notice: Subject to any disclaimer, the term of this patent is extended or adjusted under 35 U.S.C. 154(b) by 267 days.

(21) Appl. No.: 10/495,772

(22) PCT Filed: Nov. 22, 2002

(86) PCT No.: PCT/GB02/05264

§ 371 (c)(1),
(2), (4) Date: May 17, 2004

(87) PCT Pub. No.: WO03/048744

PCT Pub. Date: Jun. 12, 2003

(65) Prior Publication Data

US 2005/0001175 A1    Jan. 6, 2005

(30) Foreign Application Priority Data

Nov. 28, 2001   (EP) .................................. 01309979

(51) Int. Cl.
*G01J 3/30* (2006.01)
(52) U.S. Cl. ..................................................... 356/318
(58) Field of Classification Search .................... None
See application file for complete search history.

(56) References Cited

U.S. PATENT DOCUMENTS

| | | | |
|---|---|---|---|
| 5,127,730 A | 7/1992 | Brelje et al. | |
| 5,847,400 A | 12/1998 | Kain et al. | |
| 6,683,314 B2* | 1/2004 | Oostman et al. | 250/461.2 |
| 2003/0160184 A1* | 8/2003 | Curry et al. | 250/459.1 |
| 2003/0203492 A1* | 10/2003 | Sillman | 436/46 |
| 2003/0232445 A1* | 12/2003 | Fulghum, Jr. | 436/63 |
| 2004/0042007 A1* | 3/2004 | Osipchuk et al. | 356/318 |

FOREIGN PATENT DOCUMENTS

WO    00/50878    8/2000

* cited by examiner

*Primary Examiner*—Gregory J. Toatley, Jr.
*Assistant Examiner*—Gordon J. Stock, Jr.
(74) *Attorney, Agent, or Firm*—Dykema Gossett PLLC

(57) ABSTRACT

An optical device for directing optical signals in a fluorescence-based analyzer having first and second laser light sources for providing illuminating laser light at different wavelengths. The device comprises a band pass laser light filter associated with each laser and arranged to allow laser light of the relevant wavelength of its associated laser to pass therethrough but to reflect light of other wavelengths, each band pass filter being arranged to direct laser light from both of the lasers into a single path directed at a sample to be illuminated in use. At least two fluorescence band pass filters are provided, each of which is arranged to allow light of a selected fluorescent wavelength therethrough. The laser band pass filters are arranged to reflect fluorescent light received from the sample towards the fluorescence filters such that, in use, light received from the sample is allowed to pass through a first of the fluorescence filters if it is at a first wavelength, and through the second of the fluorescence filters if it is at a second wavelength to provide an output signals for analysis at the output of each of the fluorescence.

11 Claims, 5 Drawing Sheets

DUAL WAVELENGTH OPTICAL ANALYSER

The present invention relates to a configuration of optical elements for use in an apparatus that analyses of the relative concentration of fluorescent molecules on the surface of a work-piece.

In recent years investigating the structure of biological molecules, and in particular Deoxyribonucleic acids (DNA) and ribonucleic acids (RNA) has become a fundamental activity in biology. In particular great effort has been taken to understand the molecular structure of the human genome, which is composed of some three billion molecular units. It is felt that understanding this structure will allow more effective treatment of both congenital and infectious diseases in humans.

Once the basic structure of the genome is known it is then necessary to test the response of various elements of the genome to external influences. This field, known as functional genomics, will then map out the function and behaviour of the genome to external influences.

It will be appreciated that, even though functional genomics deals only with tiny sub-units of the whole genome, the researcher is faced with significant numbers of base units and combinations thereof, (which we generally labelled A, C, T & G)

In order to deal with the large number of possible combinations of different experiments that can be carried out, the concept of the micro-array has been developed. The micro-array consists of an array of small spots of DNA held on a substrate. Such spots are of the order of 1–100 microns in diameter. When target molecules which have various fluorescent molecules attached are washed over the spots then depending on the composition of the target solution they will bind to some spots and not others. After this process the array of spots is dried and loaded into a machine called a reader. Inside the reader light is shone onto the spots which fluoresce due to the presence of the attached molecules. Because the spatial distribution of the fluorescence over the surface of the substrate varies in response to the initial distribution of base units over the slide, from the fluorescent image it is possible to work out the composition of base units in the target solution.

This method has a number of advantages over traditional methods, the primary one being the ability to carry out a large number of independent experiments simultaneously in that each spot can be thought of as a single experiment. With current microarray techniques there can be between 50–100K spots on a single substrate which illustrates the massively parallel nature of this technique.

Thus the challenge for any reader is to produce a small focussed spot of light (generated by a laser) on the sample under investigation, then it needs to efficiently collect the resulting fluorescence from the substrate, and quantify its intensity. The laser beam needs to be point focussed onto the sample with a beam diameter of a few microns or less in order resolve the small feature sizes, which can be present on state of the art micro-arrays. Furthermore, in order to speed the data gathering process, it is the case that two laser beams of different wavelengths are scanned over the substrate, looking at two different fluorescent molecules on the arrays. Using two laser colours simultaneously more than halves the number of scans a researcher has to perform to attain the required data.

To this end the following invention seeks to provide a device which performs the following functions:

i) combining two different laser beams down a single path, and focussing the two beams on the same spot on the sample.
ii) collecting the resulting fluorescent light from the same point on the sample.
iii) selecting the relatively low level fluorescent signals from what could be an intense back scattered laser signal.
iv) separating the two fluorescent signals from each other and directing them down independent paths to be measured by separate detectors.

According to the present invention there is provided an optical device for directing optical signals in a fluorescence-based analyser having first and second laser light sources for providing illuminating laser light at different wavelengths, the device comprising:

a band pass laser filter associated with each laser and arranged to allow laser light of the relevant wavelength of its associated laser to pass therethrough but to reflect light of other wavelengths, each band pass filter being arranged to direct laser light from both of the lasers into a single path directed at a sample to be illuminated in use; and at least two fluorescence band pass filters, each of which is arranged to allow light of a selected fluorescent wavelength therethrough;

wherein the laser band pass filters are arranged to reflect fluorescent light received from the sample towards the fluorescence filters such that, in use, light received from the sample is allowed to pass through a first of the fluorescence filters if it is at a first wavelength, and through the second of the fluorescence filters if it is at a second wavelength to provide an output signals for analysis at the output of each of the fluorescence filters.

A scatter filter may be positioned in the optical path between the two fluorescence filters in order to filter out back scattered light from the laser light sources. The output of the scatter filter may be used to provide a focussing signal to control, in use, focussing optics placed between the output of the lasers and the sample to be illuminated in use.

One or more additional filters may be positioned at the output of one or more of the fluorescent filters in order to reduce the amount of interference from back scattered illuminating light that may pass therethrough.

Light received through the scatter filter, which may be positioned in the optical path between the first and second optical filters, may be passed to an illuminating intensity detecting component, which may be a light sensitive diode, to provide the focussing signal or to provide an intensity output that may be used to read a bar code associated with one or more samples.

The device may further comprise one or more optical fibres positioned in the mutual light path through which the laser light passes and returned sample light is received.

It should be noted that by using the same methodology, judiciously choosing the specification of the wavelength selective elements and extending the principles described above it is possible to construct a device with the same methodology, which uses three colours of laser on the same microarray. Such a device would further reduce the number of different experiments that a researcher needed to perform in order to arrive at the final result, thus saving significant time and cost.

The arrangement of optical elements according to the invention forms the optical core of a device for measuring the fluorescence generated by fluorescently labelled biological samples mounted on a substrate.

The device uses only bandpass optical filters, which are simpler to make lower cost and more widely available than band-stop filters. Furthermore, the device achieves all the major functions of a micro-array reader with as few as four filter elements, making the design compact and low cost.

An example of the present invention will now be described with reference to the accompanying drawings, in which.

Figure 1:
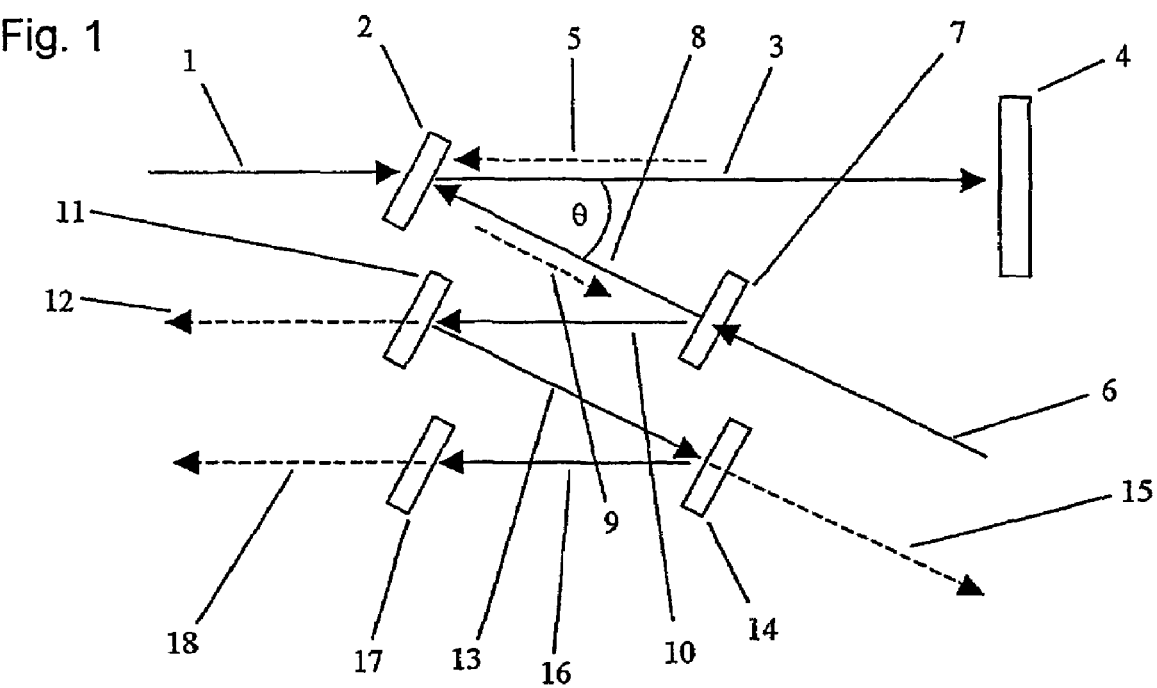
FIG. 1 is a schematic diagram showing an example of the present invention.
Figure 2:
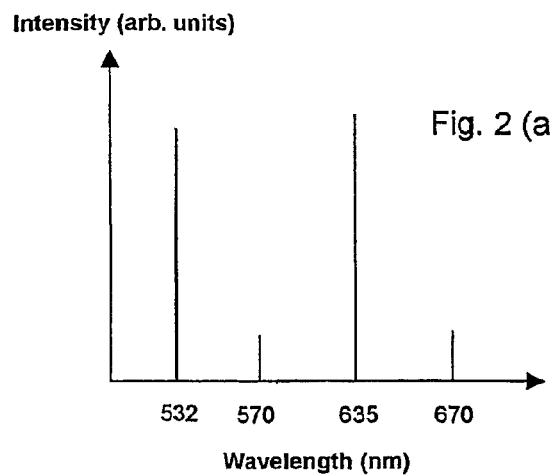
FIG. 2 is a series of graphs showing the light intensity at various components of the device of FIG. 1.
Figure 2:
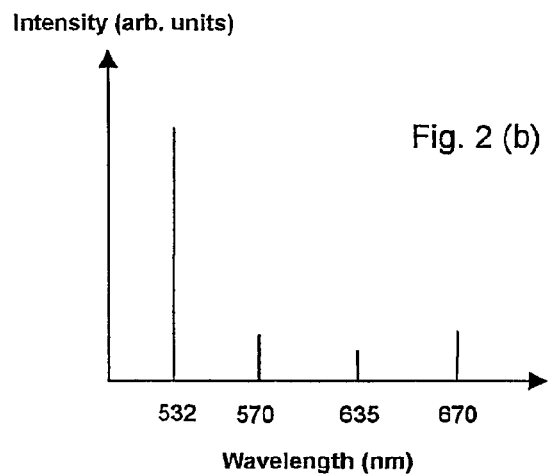
Figure 2:
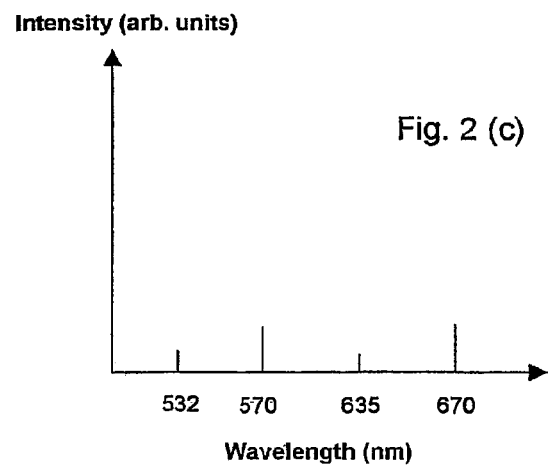
Figure 2:
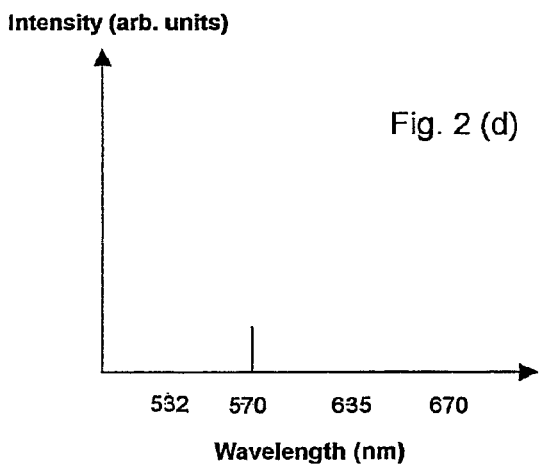
Figure 2:
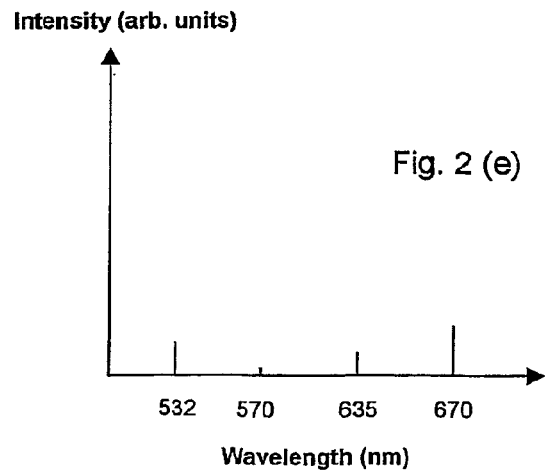
Figure 2:
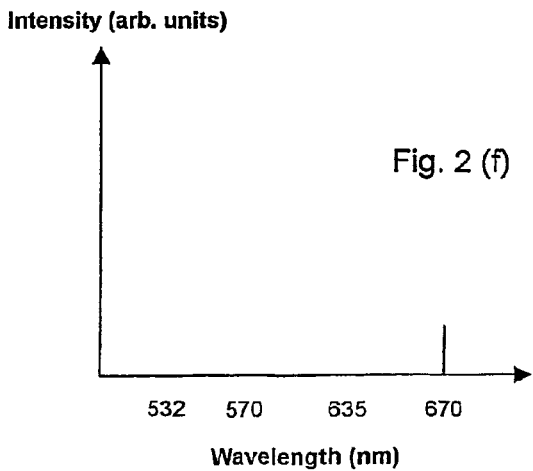

An example of the invention is shown in FIG. 1. In this arrangement there is a first path along which there is a collimated first laser beam 1, which in this example has a wavelength of 635 nm. This beam 1 passes through a first wavelength selective laser filter 2 which allows all wavelengths in the range 635±5 nm to pass through, but which reflects all other wavelengths outside this band. Therefore if spurious signals arise either from the laser generating the beam 1 or are generated along the first path, then they are reflected by first laser filter 2 by up to 99.99% and are thus excluded from an illuminating path 3 along which the beam 1 passes after passing through the first laser filter 2. Illuminating path 3 terminates at a sample 4 where the beam 1 has been focussed to generate a fluorescent signal dependent on the particular fluorescent marker (often termed 'fluorophore') being used. A commonly used marker is Cy5 which, when excited by laser height at 635 nm, produces a fluorescent light signal 5 in the region of 670 nm. This fluorescent signal 5, along with the residue of the original excitation laser wavelength, passes back down the illuminating path 3, to the first laser filter 2. FIG. 2(a) shows a schematic of the spectral content of the beam travelling along this path. The fluorescent signal 5 at 670 nm is reflected from the surface of the first laser filter 2 an angle along path 9. Conversely a large proportion (>90%) of the residual laser light from beam 1 passes through filter 2. Thus first laser filter 2 acts to reduce the amount of scattered laser light by an order of magnitude relative to the fluorescent signal 5 generated at the sample 4.

In parallel with this, a second laser light beam 6 is introduced along a second illuminating path. In this example this is a green laser beam at a wavelength of 532 nm. It passes through a second laser filter 7 which, like first laser filter 2, is wavelength selective, but which allows, in this example, all wavelengths in the range 532±5 nm to pass, reflecting all other wavelengths. Again, this filter property is useful for cleaning up the spectrum of the beam of light 6 if it has been 'contaminated' by other signals on its way to the second laser filter 7. Then the second light beam 6 passes along a path 8 to the first laser filter 2 where it is reflected off the surface and into illuminating path 3. The angle θ of path 8 relative to illuminating path 3 is such that the light beam 6 is reflected onto a path collinear with the first laser beam 1 and can thus use the same optics (FIG. 5) as the first laser for focussing onto sample 4. It is essential that θ is not too large as the reflection characteristics of the first laser filter 2 might become polarisation sensitive (the light within the current system is assumed to be depolarised) lessening the effectiveness of the first laser filter 2 at stopping light whose wavelength is outside of the pass-band of the first laser filter 2. In this example θ=30° and should always preferably be in the range of 20° to 30°. The light beam 6 excites a second fluorophore on sample 4, which in this example is Cy3; which fluoresces at 570 nm. Again, the fluorescent light 5 passes back along path 3 and is reflected off the first laser filter 2, and onto path 8 (see FIG. 2(b)), and in this case most of the residual green laser light passes through the second laser filter 7, and is effectively attenuated by 90% for any residual which passes down a path 10 toward a first fluorescence filter 11 (FIG. 2(c)). Thus, along the path 10 there are two colours of fluorescent light at 570 and 670 nm respectively and two colours of residual laser light at 532 and 635 nm.

First fluorescence filter 11 is designed to allow wavelengths in the range 570±15 nm to pass through, thus the fluorescence from the second fluorophore Cy3 is allowed to pass through first fluorescence filter 1 1 and along a first measurement path 12 relatively unhindered whilst the other three spectral components are reflected off the surface of first fluorescence filter 11 along path 13. Thus propagating along first measurement path 12 is a relatively pure beam of 570 nm fluorescence from the sample 4 (FIG. 2(d)). This can be collected and focussed onto a sensitive detector (not shown) such as an avalanche photodiode (APD) or a photo multiplier tube (PMT) where its intensity can be measured.

Subsequently the light signal travelling along path 13 impinges on an optional scatter filter 14. In this case scatter filter 14 is a selective filter with the same specification as either laser filter 2 or laser filter 7. Thus >90% of the light from one of the lasers will pass through 14, attenuating the intensity of that laser in the light that is subsequently reflected along a further path 16. The transmitted light travels from scatter filter 14 along path 15. The specification of scatter filter 14 can be chosen to compensate as appropriate depending upon which of the two exciting laser light beams 3, 4 is causing the most background in the red fluorescent detection channel. In this example scatter filter 14 has the same specification as second laser filter 7. In the position shown the scatter filter 14 has certain benefits in terms of its ability to direct light to be analysed in a preferred direction for analysis, for example, but it could be placed elsewhere in the device and achieve a similar result.

Finally the light travelling along path 16 impinges on second fluorescence filter 17 which allows light with a wavelength of 670±15 nm to pass through, forming a beam of relatively pure light emanating from the Cy5 fluorophore, which can be collected and measured by a second sensitive optical detector (not shown) (FIG. 2(f)).

Due to the spectral proximity of the lasers and fluorescent signals it may be necessary to have a sharp cut-off in the spectral response of some or all the filters used along the exit paths of the fluorescent signals (in this case fluorescence filters 11 and 17), making it necessary to use more layers of dielectric to build up the relevant filter to decrease the transmitted intensity of the out of band frequencies.

It should be noted that the wavelength selectivity of the filters 11, 14 and 17 can be interchanged without great significance. Although it is noted that the order presented here has some practical merits such as the ability to provide additional signal data for the uses described below and to optimise signal output positions, for example.

The fluorescent signals from the fluorophores on the surface of sample 4 are extremely weak in comparison to the intensity of the laser beams 1, 6 used to excite the signals. Calculations show that the intensity ratio between the laser and the fluorescent signal is generally of the order of $10^6$. Thus it is important that the residual laser beam is attenuated to a high degree in measurement paths 12 and 18, the measurement channels. Due to various practicalities of filter design and manufacture, it maybe the case that the residual laser light is attenuated by only $10^4$ times, in both measurements paths 12 and 18 thus causing a potential interference problem with the sensitive detectors.

Figure 3:
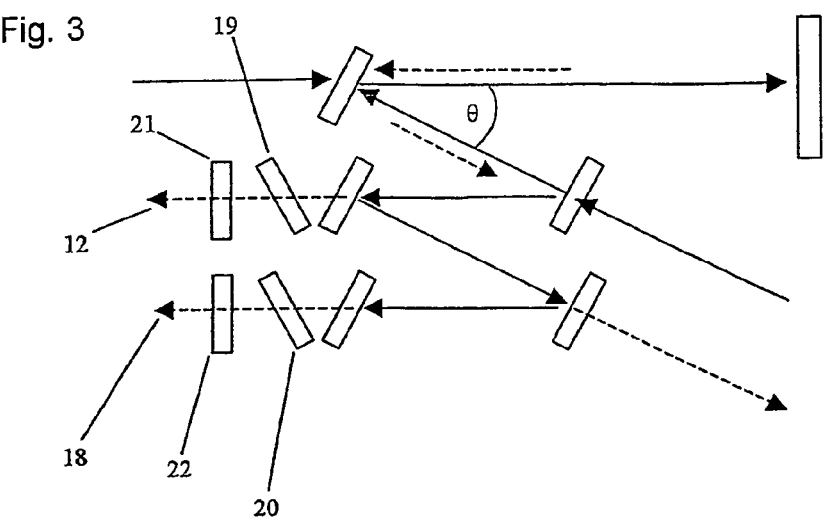
FIG. 3 is a schematic diagram of a second example of the present invention.

As such FIG. 3 Illustrates a development of the device of FIG. 1 which has extra filtration in the output channel 12 and 18. Specifically first and second additional filters 19 and 20 are placed into measurement paths 12 and 18. These filters have the same specification as fluorescence filters 11 and 17 respectively. As discussed the filters are designed to operate when the light impinges on them at an angle $\theta/2$ (=15°). It is a well know phenomenon that if two interference filters are placed sequentially with the plane of their surfaces parallel to each other then Fabry-Perot resonances can be set in the space between them reducing their effectiveness. Thus first additional filter 19 is placed at $\theta/2$ relative to measurement path 12, but not parallel to first fluorescence filter 11 in the manner illustrated in FIG. 3. This arrangement allows filters 11 and 19 to operate at optimum of combined performance. Thus filter 20 is disposed in similar manner to filter 17.

In a similar manner further filters 21 and 22 can also be disposed along measurement paths 12 & 18. These are filters designed to operate at 0° angle of incidence, and in this case one of these filters can be placed in series with the earlier filters. Such filters have the advantage that they are much more commonly available, and can in some circumstances be bought as off-the-shelf items, so are cost effective.

The addition of extra filtration introduces a further attenuation of the residual laser light (~$10^3$–$10^4$ per filter), whilst only introducing a reduction of 0.8 per filter for the fluorescent signal to be measured.

The device of the invention can be integrated into a fiber optic delivery and collection system making it convenient to deliver the light to the sample 4 and in turn collect and focus the filtered light onto the detectors.

Figure 4:
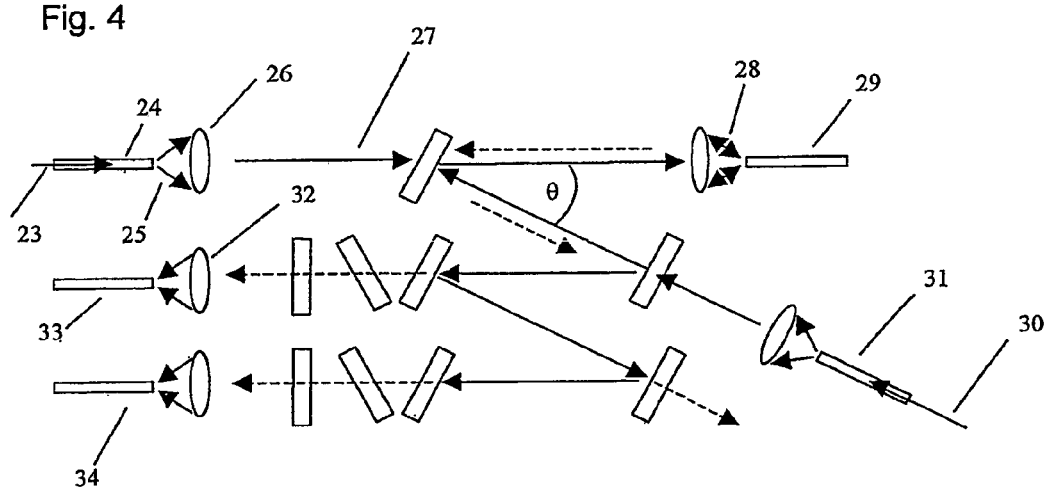
FIG. 4 is a schematic diagram showing further optional components that may be employed with the example of FIG. 3.

In this arrangement, shown in FIG. 4, the red laser light 23 is guided in an optical fiber 24, where the fiber is terminated with the red light then forming a divergent beam 25 which impinges on a lens 26 which in turn collimates the light onto a parallel beam of light propagating along path 27. Similarly the green laser beam 30 is delivered to the device using the same lens-fiber combination.

From this point the light moves through the device as described above except that a lens-fiber assembly 29, takes the laser beam energy to the sample and then collects the light travelling from the sample, thus the light cone 28 is bidirectional and consists of 4 colours of light.

The light is then directed through the device using the same arrangement of filters, except when the fluorescent light exits along measurement path 12 the light is focussed using lens 32 onto fiber 33, which carries the light to an optical detector. Likewise, the light exiting along measurement 18 is collected by a similar arrangement 34 of a lens and fiber in order to take the light off to a detector (not shown). In this all the entrance and exits to and from the device are mediated by fiber optical waveguides, allowing the device to be sighted flexibly relative to the lasers and detectors, easing overall packaging of the system.

Furthermore introducing the laser beams via fibers allows a single laser to be shared between a number of devices. For example, the device could be supplied to the end user without lasers installed on the ends of ports 24 and 31. Then the end user either has or buys a laser which has a number of fiber coupled optical outputs, at which point laser light is introduced by coupling one of these outputs to the input ports 24 or 31. In this way the complexity and overall cost of installing the device of the invention can be reduced as one 100 mw laser can supply 10 or more independent sets of apparatus. This feature is particularly useful for installation where many devices are installed side-by-side.

Figure 5:
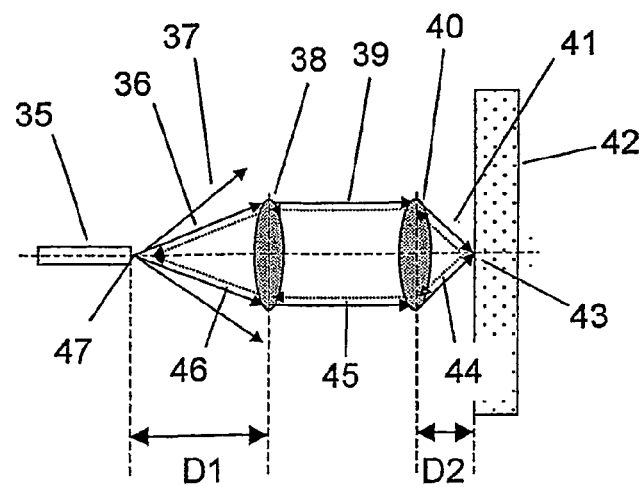
FIG. 5 is a schematic diagram of a focussing component that may be employed with the apparatus of the present invention.

FIG. 5 shows an example of a focussing system for use with the present invention. This system is a means of coupling light from the optical fiber 35 onto a semi-transparent work-piece 42, where a fluorescent compound is placed at point 43, which is excited by the light, and as a consequence emitting fluorescent light which in turn is collected by the optical system and passed back down the same optical fiber, whereby a feedback signal is generated which enables the user to measure how well the device is focussing the light onto the work-piece 42. This forms the basis of an automatic system for optimising the distance between an objective lens 40 and the work-piece 42.

In use, one or multiple laser beams 1, 6 are transmitted down the optical fiber 35. In this case the fiber is standard telecommunications grade fiber and, for example, the fiber could be a 50/125 micron (core/cladding) diameter fiber with a numerical aperture (NA) of 0.2. The fiber is terminated by a planar cleaved or polished face and thus to a first approximation the laser energy would be distributed over a disk 47 of 50 microns, radiating out in a cone 37 with a half angle of ~11.5°. The light then impinges on a first lens 38, spaced from the end of the fiber by a distance generally equal to its focal length. In this case the lens 38 is an aspheric lens, optimised for the wavelengths of light passing through the lens. To take an illustrative example, lens 38 could be a p/n 350260 lens made by Geltech Inc. Here the lens has a NA of 0.16, thus it only accepts light from a narrower cone 36 which has a half angle of ~9.2°, hence there is some overspill of the light coming out of the fiber but, as will be discussed below, this is not important to the overall performance of the device. As a result of the light passing through lens 38, it forms a parallel beam 39 which passes onto objective lens 40. In this case it is desirable to maximise the NA of objective lens 40 in order to achieve two goals. Firstly, by making the NA of objective lens 40 greater than that of lens 38, demagnification of the image of disk 47 will be achieved on the work-piece 42 at point 43. Secondly by maximising the NA of objective lens 40, the amount of fluorescent light collected will be maximised, increasing the signal to noise ratio.

It will be appreciated that it is possible to use different diameters of fibre for the fibre 35, and by changing the diameter and/or the properties of lenses 38 and 40 it is possible to adjust the size of the illuminating spot on point 43 to optimise the performance of an analyser employing the device in terms of its ability to extract information from the surface of the substrate 42.

Thus as an example objective lens 40 could be p/n 350330 from Geltech Inc, which would reduce the size of the projected image of disk 47 on the work-piece 42 by 4.3×, (~11.6 micron diameter) and would subtend ~27% of all of the available solid angle.

Objective lens 40 focuses the light into a converging cone 41 onto the work-piece 42, at point 43. It is at this point that the fluorescent signal is generated by the sample deposited on the front surface of work-piece 42, being collected by objective lens 40 as a diverging cone of light 44, which is in turn collimated into a parallel beam 45 by objective lens 40, and then focussed by lens 38 into a converging cone 46 where it is coupled back into fiber 35 and then propagates back along fiber 35 in the direction opposite to the initial laser beams 1, 6.

It should be noted that when coupling light back into the fiber 35 it is crucial that the NA of lens 38 is less than or equal to the NA of fiber 35, in order to ensure that all the fluorescent signal is coupled back into fiber 35 with little or no wastage due to over-spill. This is because it is essential to minimise the amount of laser energy needed to collect a given amount of fluorescent signal, as high laser intensities for prolonged periods tend to damage the fluorescent compounds deposited on work-piece 42 making them less efficient as time goes by. When coupling light out of fiber 35 into lens 38, a low efficiency of collection of light by lens 38 can be offset by increasing the power of the laser to compensate, as there is usually more than a sufficient margin of excess laser power available.

As discussed before it is the case that the propagating light is composed of the fluorescent light generated by the molecules at point 43 and a residue of the initial laser beams used to excite the fluorescence. The laser residue has a number of causes. For example, blemishes on the surface and within the body of work-piece 42, plus a reflection of 4% back along the path caused by the impedance mismatch between the body of work-piece 42 which has a refractive index of ~1.5 and air which has a refractive index of ~1. As such there will always be a minimum amount of the exciting laser beams travelling back along fiber 35.

Figure 6:
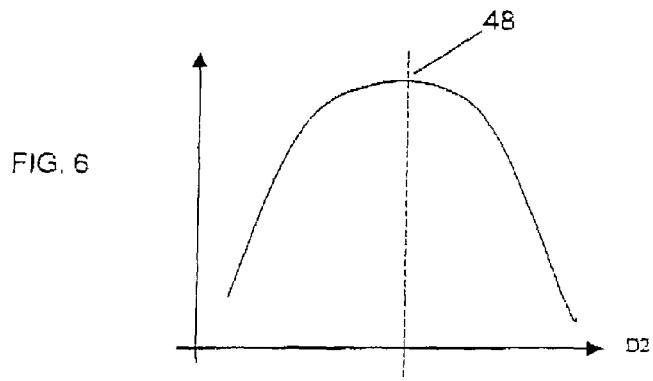
FIG. 6 is a graph showing intensity of light received by the apparatus of the invention.

It is the case that the image of disk 47 at point 43 is due to the distance of lens 38 from disk 47 (D1) and objective lens 40 from point 43 (D2). In this device D1 is fixed and thus only D2 can vary. Thus by measuring the amount of laser light propagating along fiber 35 it is possible to tell how well optimised D2 is. Specifically FIG. 6 shows the response curve for the system as D2 is varied, and at the optimum focus of objective lens 40 relative to point 43 the intensity of the light transmitted back down fiber 35 is seen to reach a maximum 48, and on either side of maximum 48 the intensity decreases.

Figure 7:
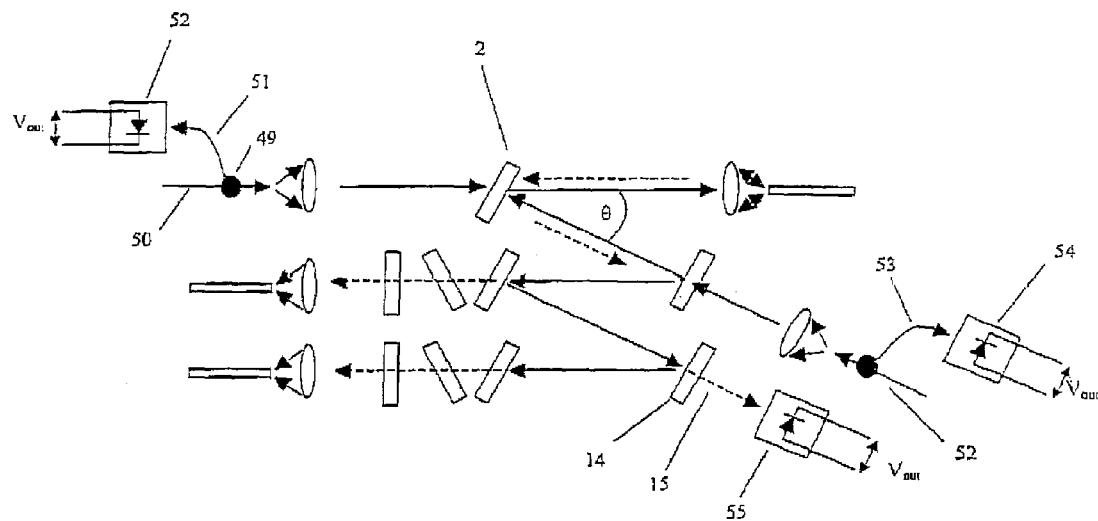
FIG. 7 is a schematic diagram showing the example of FIG. 3 further adapted to provide a focussing control signal.

In practice this signal could be detected at a number of different points in the equipment. The primary place is back down the fiber 35 in the device shown in FIGS. 1, 3, 4 and 7. Referring now to FIG. 7, the green or the red laser light is coupled into the example apparatus described above and one of the returned laser beams has a path out of the device along path 15. Thus FIG. 7 shows example options for detecting the reflected laser light. In one option the optical fiber 24 has a directional coupler 49 inserted which allows the reflected laser light to pass back through onto a photoelectric sensor 52. As it is sited behind first laser filter 2, only a single frequency of laser energy will tend to propagate back up this arm. The voltage $V_{out}$ across sensor 52 will be proportional to the intensity of the light being reflected from the work-piece 42 and thus can be used to generate the autofocus signal as shown in FIG. 6

Likewise a similar arrangement can alternatively be placed along fiber 31 where the other laser frequency is introduced where the other colour of reflected laser light is directed to a detector 54.

Siting the photodectors 52, 54 along the fibres 24, 31 into which the laser energy is introduced into the device may be prone to the signal coming back off the sample being weak in comparison to stray light being introduced to the detector directly from a laser 1, 6. Thus it is also possible, as an alternative, to site a detector 55 along path 15, which has no laser. Siting the photoelectric sensor here allows the light to be directly shone onto the photosensitive area of the sensor 55 from free space, dispensing with the need for a connecting fiber. Thus saving cost and potentially increasing the signal received by sensor 55.

The output from sensor 52, 54 or 55 can then be used to generate a control signal which in turn is used to drive a servo motor system which continuously varies distance D2 in order to optimise the fluorescent signal being measured. This is highly desirable because in practice the work-piece 42 will not be flat or have uniform thickness. Thus as the lens arrangement moves across the surface of work-piece 42, D2 will always be changing. Such real time control of distance D2 ensures that the quality of the fluorescent image generated by the device is optimal under all conditions.

For high throughput DNA screening there is a large amount of data which needs to be quickly and efficiently catalogued. As a result there is a trend to mark the substrates with bar codes. This allows the substrate to be identified all the way through its useful from its initial creation, to the printing of the micro-array and finally to the hybridisation and reading. The following illustrates how a bar code can be read using the example of the invention without any extra equipment needing to be added.

Figure 8:
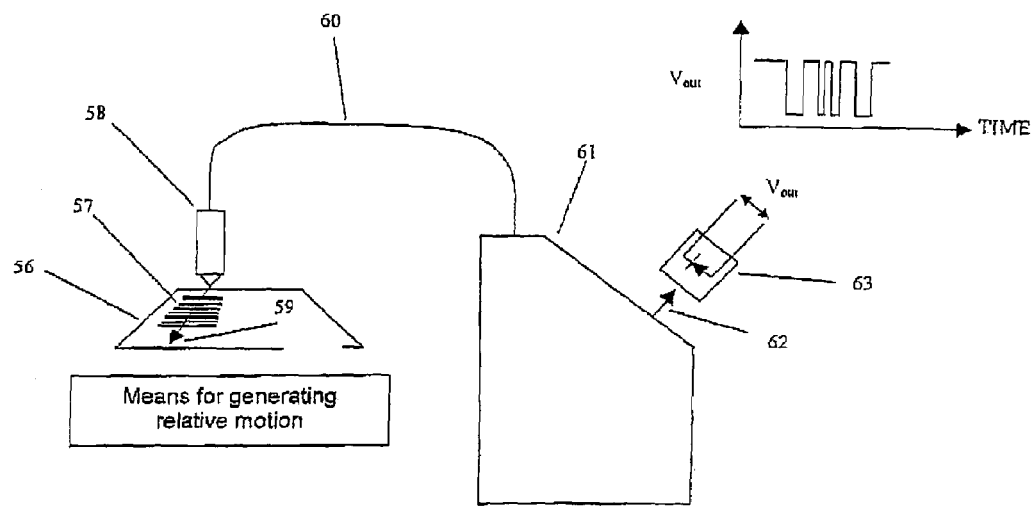
FIG. 8 is a schematic diagram of an example of the present invention employed to read a bar code associated with an array of samples to be illuminated.

FIG. 8 illustrates a possible configuration of such a device. In this case all the detection electronics used to read the weak fluorescence signals discussed above is switched off, along with one of the lasers 1, 6 and thus for the purposes of this discussion it is the second (green) laser 6 which is used to scan over bar-code 57. Therefore in this case a substrate 56 with a pre-printed bar code 57 is loaded into a machine employing the invention and the substrate is passed underneath the optics of the examples above in FIG. 5, here denoted by number 58. By traversing path 59 the bar code 57 is scanned past the focal point of optics 58, and thus a time varying amount of laser light that is reflected from bar code 57, collected by optics 58 and passed along the of optical fiber 60 back to the spectral optics 61 as illustrated in FIGS. 1–7. As a result of including the focus system as illustrated in FIGS. 5–7, the green laser light exits the spectral optics along a path 62 and impinges on a detector 54 positioned as shown in FIG. 7. A time varying voltage will be seen on its output (see inset) which, if the substrate 56 is driven at constant speed, will mean that the information content of the bar code 57 can be read by suitable hardware and software.

Figure 9:
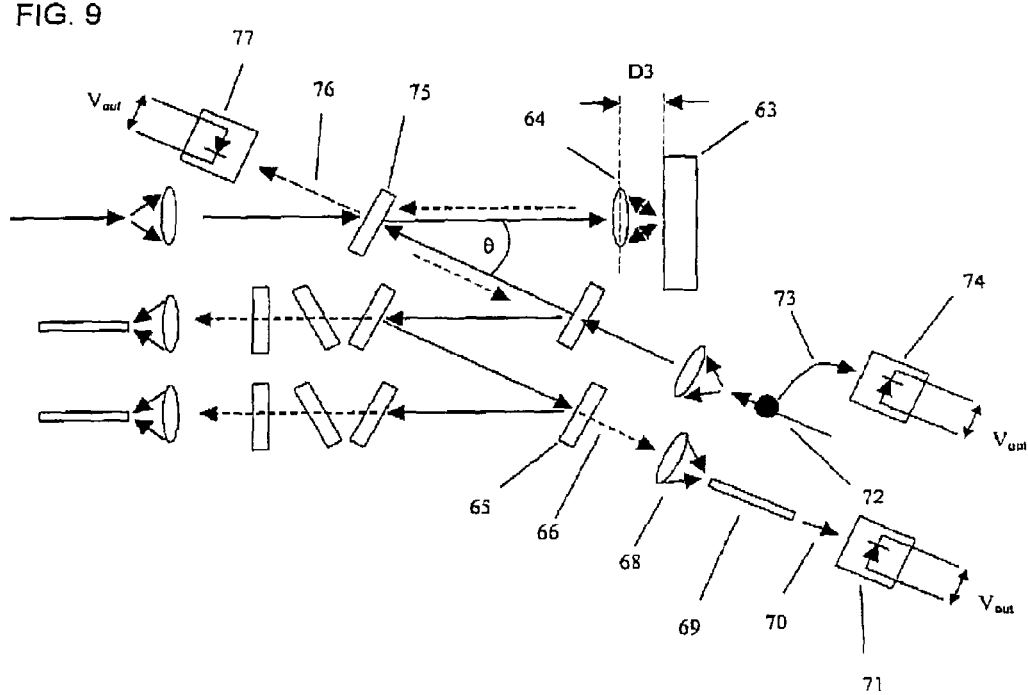
FIG. 9 is a schematic diagram showing the example of FIG. 7 further adapted to provide a laser power monitoring signal and a second example focussing component.

It should be noted that in this case the focal distance of optics 58 to substrate 56 is less critical than when the high-resolution fluorescence is being detected thus the focus function is not necessary, and the components can perform this dual, function. FIG. 9 shows an alternative arrangement that uses the same methodology for generating the autofocus signal but does not use the arrangement detailed in FIG. 5 to introduce the light to and collect it from the sample.

FIG. 9 shows an apparatus of the same construction as detailed in FIG. 1, where a sample 63 with a fluorescent marker is disposed adjacent to the device and a parallel beam of light in the device is focussed down to a spot on 63 by a converging lens 64. In this case a mixture of the fluorescent light and reflected laser beam 64 passes back through the device until it reaches a filter 65 with the specification of laser filter 2 or 7.

Dependant on the specification of filter 65, the beam 66 is composed of the laser light that is reflected off the surface of lens 64, where this parallel beam passes through lens 68 which again is a converging lens that focusses the light onto the end of fibre 69 which transmits the light via freespace beam 70 to the detector 71 which is used to form the same output signal $V_{out}$ as used in the example of FIG. 6. In this case the image of the light spot on sample 63 is aligned with the end of fibre 69 and one to one imaging is achieved. As such optimum power coupling is coupled into fibre 69 when the spacing D3 between 63 and 64 is equal to the focal length of lens 64. Similar to the above example, by changing D3 and monitoring the $V_{out}$ of detector 71 the optimum value for D3 can be acheived and maintained if sample 63 tends to move relative to lens 64 as it is raster scanned under lens 64.

There are other options for sitting the detector. In FIG. 9 item 72 is one of the fibers used to introduce one of the colours of laser light into the device. It is the case that if a branched 1-2 coupler is used instead of a plain piece of fiber then the returning laser light 73 is coupled back into detector 74 and a portion of the returning laser light 75 can be coupled up into the detector 76 and act to produce a suitable signal for an autofocus system. It should be noted that the use of detector 74 will most likely lead to loss of laser power introduced into the device and thus will affect the overall performance of the system.

Using this method does have operational advantages over the use of an intermediate fiber. Primarily this relates to the distinctiveness of the $V_{out}$. In the scenario presented in the preceding paragraph the amount of laser light reflected off 63 is ~4% for a glass-air interface where the glass has refractive index of ~1.5. As there is no intermediate fiber between the device and sample 63, then in this case there are the minimum number of optical surfaces between the sample and fibre 69.

Here this leads to 80% of the signal focussed on fibre 69 being composed of light from the interesting glass-air reflection of sample 63. This compares to the situation when there is a fiber interposed between sample 63 and lens 64 plus the set of optics as illustrated in FIG. 5 where the surface reflected light from sample 63 comprises less than 33% of the signal at the detector as the fiber ends and the extra lenses will contribute >2× as much light as the surface reflection and these other components will not change with D3, and thus the electrical signal illustrated in FIG. 6 will sit on a constant background that is 2× as big as varying signal. Hence the electronics used to optimise the value of D3 will find it easier to detect the optimum condition without the presence of the fiber.

It should be noted that in order to optimise the amount of light collected by the detection of either the fluorescence or the autofocus light it is necessary to match NA and diameter of lens 64 to the lenses used to couple light into the fibers. In this case to optimise the amount of scattered fluorescent light collected from the sample it is necessary that the NA of lens 64 is as large as possible and in practical terms this should be >0.6. In contrast the light used to couple light into fibre 69 should not have an NA greater than that of the fiber thus the result is that the NA of lens 68 and all other similar lenses should be in the range 0.12–0.2.

For a number of reasons it may be desirable to be able to monitor the power of the laser beam being introduced to the block in real time. In order to do this with no appreciable loss of signal the arrangement out lined in FIG. 9 could be employed. Here item filter 75 is identical to filter 2 as previously described. As the laser beam passes through filter 75, a small amount of the power will be reflected off the surface and coupled back along path 76 toward an optical detector 77. This can be as low as 0.2% if the correct multi-layer coatings are applied to filter 75, but even at this small fraction it is still low enough to comfortably be detected by even a simple detector such as a silicon PIN diode.

By having a direct measurement of the laser power introduced into the block a number of uses can be made of it. In the short term if the laser power fluctuates over one scan then the changes that this will introduce to the intensity of the fluorescence detected can be corrected for in first order. Secondly as the laser ages in normal use, this signal can be used as a means of monitoring the power drop and flagging up a warning when the power in the device has dropped below acceptable levels and as a result the laser needs replacing.

The energy reflected in this manner is intrinsic, but utilising it in this way does not introduce any extra optical elements into the beam and hence extra loss making it an efficient method of introducing such a feature. Furthermore this method of monitoring can be used throughout the device and is not limited to the position illustrated.

In many fields of study, in particular studies of living organisms, it may be advantageous to use different coloured fluorophore stains to highlight different chemicals, or chemical processes taking place within the cells. These have to be excited using different colours of excitation energy, and the images then formed have to be separated according to colour. This can be accomplished in two ways; in the first the singular beam in the system described so far can be scanned over the surface of the sample to form an image from a raster pattern. Secondly the sample can be imaged as is done in a microscope in order to detect the resulting fluorescence. As the device structure described preserves the spatial information contained in the light beam, the principles for combining and separating the different components can be used in multi-fluorophore imaging systems such as a microscope.

Figure 10:
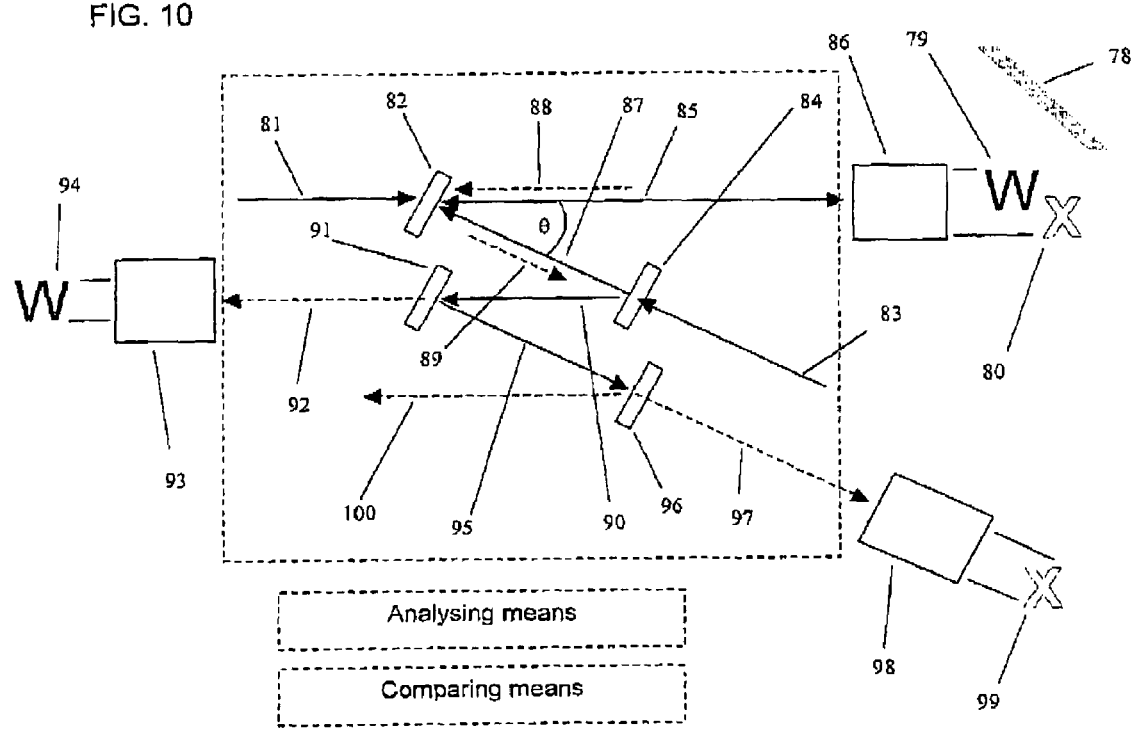
FIG. 10 is a schematic diagram and a further example of the present invention.

Such a device is illustrated in FIG. 10. In this configuration the device is pointed at a substrate 78, on which there are spatially different distribution of fluorescent dye which for illustrative purposes are shown as a 'W' (79) and a 'X' (80). Specifically the dyes that compose 79 and 80 are excited by $\lambda_{ew}$ and $\lambda_{ex}$, and fluoresce at $\lambda_{fw}$ and $\lambda_{fx}$ respectively. In this arrangement $\lambda_{ew}$ is fed into the device along path 81 passing through the bandpass filter 82. Likewise $\lambda_{ex}$ is fed in along path 83, passing through bandpass filter 84. Both filter 82 and filter 84 are tuned to pass a narrow band of wavelengths centred on $\lambda_{ew}$ and $\lambda_{ex}$ respectively with 5–10 nm width. Outside this range all the light is efficiently reflected. Then $\lambda_{ew}$ beam progresses along path 85 to a set of optics 86 the images the parallel laser beam onto substrate 78. In parallel $\lambda_{ex}$ is transmitted along path 87, bounces of the surface of filter 82 and then directed to optics 86 via path 85. In this case 85 could be similar in form to an optical microscope, comprising the microscope objective being disposed at the correct distance from the sample to form an image, and the associated optics to convert the image into a parallel (or nearly parallel) beam of light that is suitable for feeding into the front end of the invention herein described.

At this point 79 and 80 are excited and emit light at $\lambda_{fw}$ and $\lambda_{fx}$ respectively which is collected by optics 86 which converts the images into parallel beams of light which are transmitted back along path 88. At this point the beam comprises the images of 79 and 80 at $\lambda_{fw}$ and $\lambda_{fx}$ plus residual laser excitation at $\lambda_{ew}$ and $\lambda_{ex}$. As the beam reflects off filter 82, and then travels along path 89 then off filter 84, both $\lambda_{ew}$ and $\lambda_{ex}$ are attenuated by ~10× as filter 82 and filter 84 are transparent to $\lambda_{ew}$ and $\lambda_{ex}$ respectively allowing the majority of the power at these wavelengths to pass through the filter. As the beam is reflected off filter 84, it then passes along path 90 to filter 91. Here for the purposes of illustrating the invention filter 91 is a band pass filter tuned to allow wavelengths in the region $\lambda_{fw}$ to pass. Thus after filter 91 beam 92 contains only the spatial information encoded by 79, where this passes to a set of optics 93 which forms an image 94 of 79 at $\lambda_{fw}$. As stated above, keeping the analogy with an imaging microscope, 93 could be similar in form to the eyepiece of a microscope or the necessary optics that are used to project micrographs onto the photosensitive area of a camera. The image can be detected by a range of imaging sensors such as the human eye or more likely a spatial sensitive electronic detector such as a CCD or CMOS sensor. In parallel to this the light at $\lambda_{fx}$ and as a consequence the spatial information encoded in 80 is reflected off the filter 91 and passes along path 95 toward filter 96. In the same sense as filter 91, filter 96 allows all frequencies in the region of $\lambda_{fx}$ to pass whilst reflecting all other. Hence the spatial information contained within 80 passes along path 97, toward optics 98, which is similar to optics 93, in that it is a set of optics which forms an image 99 of 80.

The major advantages of this device are that it is the most efficient method of splitting multi wavelength images from a single composite target. Again it should be noted that the device structure described is scalable, and that the beam 100 reflected off 96 can contain images at other wavelengths which can be split by a similar arrangement of filters as that comprising 82, 84, 91 & 96.

The invention claimed is:

1. An optical device for directing optical signals in a fluorescence-based analyser having first and second laser light sources for providing illuminating laser light at different wavelengths, the device comprising:
   a band pass laser filter associated with each laser and arranged to allow laser light of the relevant wavelength of its associated laser to pass therethrough but to reflect light of other wavelengths, each band pass filter being arranged to direct laser light from both of the lasers into a single path directed at a sample to be illuminated in use; and
   at least two fluorescence band pass filters, each of which is arranged to allow light of a selected fluorescent wavelength therethrough;
   wherein the band pass filters are arranged to reflect fluorescent light received from the sample towards the at least two fluorescence band pass filters such that, in use, light received from the sample is allowed to pass through a first of the at least two fluorescence filters if it is at a first wavelength, and through the second of the at least two fluorescence filters if it is at a second wavelength to provide output signals for analysis at the output of each of the at least two fluorescence filters.

2. The optical device according to claim 1, further comprising a scatter filter for filtering out back-scattered laser light.

3. The optical device according to claim 2, wherein the output of the one of the band pass laser filters or the scatter filter is used to provide a monitoring signal.

4. The optical device according to claim 3, wherein the monitoring signal is fed to a focussing device associated with the output of the optical device to provide control thereto.

5. The optical device according to claim 3, wherein the monitoring signal is fed to a processor which analyses the monitoring signal to provide an output indicative of a bar code that is scanned by at least one of the laser light beams in use.

6. The optical device according to claim 1, wherein one or more additional filters are positioned at the output of one or more of the at least two fluorescent band pass filters in order to reduce an amount of interference from back scattered illuminating light that may pass therethrough.

7. The optical device according to claim 1, further comprising one or more optical fibres positioned in the light path through which the laser light passes and returned fluorescent light is received.

8. An optical fluorescent-based analyser comprising:
   a first and a second laser light source arranged to emit laser light at differing wavelengths;
   the optical device according to claim 1 coupled to the laser light sources; and
   analysing means associated with the outputs of each of the at least two fluorescence band pass filters to provide fluorescence data based thereon.

9. The optical fluorescent-based analyser according to claim 8, further comprising means for monitoring the power laser light introduced, in use, to the optical device, and means responsive to the laser light and received fluorescent light levels for producing a control signal.

10. The optical fluorescent-based analyser of claim 8, further comprising means for focusing the output laser light, in use, on a sample; and
   means for generating relative motion between scanning light and the sample to be scanned in use.

11. The optical fluorescent-based analyser according to claim 8, arranged to separate multiwavelength images from a single composite target according to their individual wavelengths.

* * * * *